(12) United States Patent
Aigaki

(10) Patent No.: US 6,563,018 B2
(45) Date of Patent: *May 13, 2003

(54) GENE SEARCH VECTOR AND GENE SEARCH METHOD

(75) Inventor: Toshiro Aigaki, Tokyo (JP)

(73) Assignee: Japan Science and Technology Corporation, Saitama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,520

(22) Filed: Jan. 14, 2000

(65) Prior Publication Data

US 2002/0032913 A1 Mar. 14, 2002

(51) Int. Cl.[7] ................... C12N 15/00; C12N 15/63; A01K 67/00; C07H 21/04

(52) U.S. Cl. ..................... 800/22; 800/25; 800/8; 800/13; 800/3; 435/320.1; 435/455; 536/23.1

(58) Field of Search ................ 800/22, 25, 8, 800/13, 3; 536/23.1; 435/320.1, 325, 455

(56) References Cited

PUBLICATIONS

G. Toba et al., "The gene search system: A method for efficient detection and rapid molecular identification of genes of *Drosophila melanogaster*", Genetics Society of America, 151, pp. 725–737, Feb. 1999.

P. Rorth, "A modular misexpression screen in *Drosophila* detecting tissue–specific phenotypes", Proc. Natl. Acad. Sci, vol. 93, pp. 12418–12422, Oct. 1996.

*Primary Examiner*—David Guzo
*Assistant Examiner*—Quang Nguyen
(74) *Attorney, Agent, or Firm*—Wenderoth, Lind & Ponack, L.L.P.

(57) ABSTRACT

The present invention provides a gene search method comprising P-element insertion and being capable of efficiently identifying a novel gene regulating various biological functions of Drosophila and specifying a function corresponding to the novel gene. An unknown gene of Drosophila can be searched by the method comprising a step of inserting in the genome of Drosophila a gene search vector carrying two sets of an expression regulatory sequence comprising UAS sequence for GAL4 transcription factor GAL4 and a promoter sequence, as integrated in the P-element sequence in such a manner that their downstreams are in opposite directions, mating the vector-inserted Drosophila with a Drosophila expressing the GAL4 to create progeny individuals, and identifying a vector-inserted line with a phenotype different from those of wild-type Drosophila, and determining the nucleotide sequence of the gene for the mutant phenotype.

9 Claims, 2 Drawing Sheets

FIG. 2a

```
Drosophila Rap2    1 MREFKVVVLGSGGVGKSALTVQFVSGCFIEKYDPTIEDFYRKEIEVDSSPICVLEILDTAG  60
Human Rap2         1 MREYKVVVLGSGGVGKSALTVQFVTGTFIEKYDPTIEDFYRKEIEVDSSPSVLEILDTAG  60

Drosophila Rap2   61 TEQFASMRDLYIKNGHGFIVMYSLTNHQTFQDISSMKNVITRVKGSQPAPILLVANKFIDL 120
Human Rap2        61 TEQFASMRDLYIKNGQGFILVYSLVNQQSFQDIKPMRDQIIRVKRYEKVPVILVGNKVDL 120

Drosophila Rap2  121 DCQREVSTAEGNALAQLWDCPFIEASAKDRINVNEVFATIVRIEMNLTQENRQKKNYCC-- 178
Human Rap2       121 ESEREVSSSEGRALAEEWGCPFMETSAKSKTMVDELFAEIVRQMNYAAQ-PDKDDPCCSA 179

Drosophila Rap2  179 CTLL 182
Human Rap2       180 CNIQ 183
```

FIG. 2b

```
Drosophila mGST    1 MASPVELLSLSNPVFKSFTFWVGVLVIKMLLTAIQRFNTKTFANPED-LMSPK-LK     58
Human Rap2         1 MVD-LTQV-MDDEVFMAFASYATIILSKMMLMSTATAFYRLTRKVFANPEDCVAFGKGEN  58

Drosophila mGST   59 V-KF--DDPNVERVRRAHRNDLENILPFFAIGLLYVLTDPAAFLAINL-LFRA-VGIARIV 113
Human Rap2        59 AKKYLRTIDDRIVERVRRAHLNDLENIIPFLGIGLLYSLLSGPDPSTAIL-LHFRLFVG-ARIY 116

Drosophila mGST  114 HTLVYAVVVPQPSRALAFFVALGATVYMALQVIASAAF-         152
Human Rap2       117 HTIAY-LTPLPQPNRALSFFVGYGVTLSMAYRLLKSKLYL        155
```

GENE SEARCH VECTOR AND GENE SEARCH METHOD

BACKGROUND OF THE INVENTION

1. Field of the Invention

The present invention relates to a novel gene search vector for efficiently detecting an unknown gene of a fly, Drosophila, and a gene search method using the vector.

2. Description of the Related Art

Rapid progress has been made in the determination of the full-length genome sequences of various species. So as to effectively utilize the information about these genome sequences, a current investigative issue is the identification of a specific sequence domain practically responsible for a biological function to sequentially determine such domains in the form of "gene" corresponding to biological function.

The essential mechanisms of biological functions are preserved in any species, and genes allowing the mechanisms to function are also analogous in any species. Based on such grounds, the functional elucidation of a gene of a model lower organism is applicable to other numerous organisms including humans. The gene is for example life-span regulatory gene. The evidence up to date indicates that life span characteristically has a close relation with stress resistance, anti-oxidative action and biological protective potency. Because these functions are regarded to belong to the principal mechanisms of any species, the elucidation of the mechanisms in a model organism and the findings about the factors and genes involved in the mechanisms are of significant importance in various industries. For example, it is expected that life-span prolonging factor and stress-resistance factor not only provide information useful for the development of medicinal products but also are directly involved in the development of foodstuffs helping and supporting the control and promotion of human health (foodstuffs enriched with such factors and foodstuffs containing ingredients facilitating the generation of these factors in living organisms). It is also expected that industrially useful animals and plants, given with these ingredients in the forms of feeds or fertilizers or integrated with genes encoding these ingredients, can yield an improved productivity. Furthermore, factors capable of regulating the appearance and growth of insects or the propagating actions thereof provide new strategies for the control of the reproduction of useful insects or harmful insects with deep relation to agriculture and forestry. Otherwise, factors triggering cell growth or differentiation and abnormal actions provide valuable information for the molecular understanding of the fundamental pathogenesis of human genetic diseases or the functions of organisms; and these factors additionally serve as potent materials for the therapies of cancer and nerve diseases and for the development of novel drugs for these diseases.

Drosophila has traditionally been used frequently as a material for genetic research works and is endowed with powerful analytical modalities in the fields of genetics and molecular biology. Thus, Drosophila has been acclaimed as an excellent model organism for searching novel gene. In a practical sense, many novel genes including "homeobox gene" have been isolated from Drosophila.

The mutagenesis process comprising inserting the transposon P-element into the genome has been known as the means for searching novel genes in Drosophila (Science 239: 1121–1128, 1988; Proc. Natl. Acad. Sci. USA 92:10824–10830, 1995).

However, the frequency of the occurrence of a homozygote phenotype recovered through such mutagenesis using P-element is as low as about 15%, which is not sufficient for the detection of a gene in the genome (Science 239:1121–1128, 1988). It is considered that this is due to the facts that the sites for P-element insertion are mostly in the upstream of the coding sequence (Proc. Natl. Acad. Sci. USA 92:10824–10830, 1995) and that the genome per se is functionally redundant (Cell 86:521–529, 1996). Additionally, it is also indicated that the resulting phenotype sometimes has no relation with P-element insertion (Genetics 147:1697–1722, 1997).

As means for the expression of a gene of Drosophila in an enforced fashion further, a method has been known, comprising inserting in the Drosophila genome a vector carrying UAS (upstream activator sequence) enhancer as the target sequence of a yeast-derived GAL4 transcription activator, mating the transformed Drosophila with a Drosophila capable of expressing GAL4 (GAL4 expression line) to create a progeny individual, and allowing the progeny individual to express a gene downstream of the UAS enhancer (Development 118:401–415, 1993).

Another method using a combination of the GAL4-UAS enhancer compulsory expression system and the mutation induction with P-element insertion has been known (Proc. Natl. Acad. Sci. USA 93:12418–12422. 1996. Dros. Inf. Serv. 80;90–92, 1997). According to the method, a pair of the UAS enhancer/promoter is integrated in the multicloning site of a P-element transformation vector pCa SpeR (Gene 74:445–456, 1988) on the side of 3' P-element; Drosophila with the vector inserted therein is mated with the GAL4 expression line, to enforce the expression of genes downstream of the vector insertion site in a progeny individual to identify phenotypes and the genes corresponding thereto.

The method using a combination of the GAL4-UAS enhancer forced expression system and the mutagenesis with P-element insertion is excellent in that genes can be detected on the basis of gain-of-function phenotype and loss-of-function phenotype. However, the occurrence of the mutant phenotype caused by P-element insertion is so low by the method. Hence, means or methods capable of efficiently allowing a mutant phenotype to emerge have been desired so as to detect a great number of useful novel genes.

In such circumstances, the invention has been accomplished for the purpose of providing a novel gene search vector capable of efficiently identifying a novel Drosophila gene in a manner so as to specify the function corresponding to the novel Drosophila gene; and a gene search method.

SUMMARY OF THE INVENTION

The present invention provides a gene search vector, which carries P-element sequences and two sets of an expression regulatory sequence comprising a UAS sequence for GAL4 transcription activator and a promoter sequence, wherein the expression regulatory sequences are integrated in the P-element sequence in such a manner that their downstreams are in opposite directions.

In one preferable embodiment of the gene search vector, the promoter is the core promoter of heat shock protein hsp70 gene.

In the other preferable embodiment of the gene search vector, the two sets of the expression regulatory sequence are independently integrated in the 5' P-element sequence and 3' P-element sequence.

In another preferable embodiment of the gene search vector, a marker gene is present between the two sets of the expression regulatory sequence, while Drosophila white gene is used as the marker gene.

In a still further embodiment of the gene search vector, the full length of the vector DNA is less than 8 kbp.

The present invention also provides a fly carrying the gene search vector set forth above being integrated in the genome thereof.

The present invention further provides a method for searching an unknown gene of Drosophila, comprising the steps of:

(a) inserting the gene search vector of any one of claims 1 to 6 into the genome of Drosophila, (b) mating the vector-inserted Drosophila with a Drosophila expressing the GAL4 transcription activator to create progenies, and identifying a vector-insertion line with a phenotype different from those of wild-type Drosophila, and (c) determining the nucleotide sequence of the gene for the phenotype of the mutant individual.

In one preferable embodiment of the gene search method, in step (c), a mRNA fragment including mRNA transcribed from a partial sequence of the gene search vector is amplified by reverse-transcriptase-polymerase chain reaction method to determine the nucleotide sequence of the resulting amplified DNA.

BRIEF DESCRIPTION OF THE DRAWINGS

FIGS. 2a and 2b show the comparison in the putative amino acid sequences of Rap2 gene and mGST gene between humans and Drosophila.

DESCRIPTION OF THE PREFERRED EMBODIMENTS

Figure 1A:
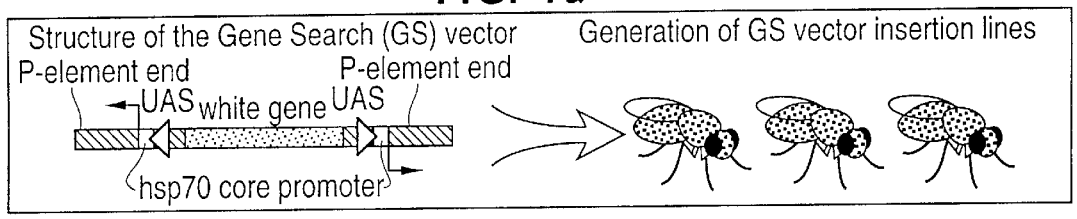
FIGS. 1a, 1b and 1c show a schematic view depicting the inventive method.

As shown in FIG. 1a, for example, the gene search vector (sometimes referred to as "GS vector" hereinafter) comprises two sets of an expression regulatory sequence of the UAS enhancer and an appropriate promoter sequence (for example, the core promoter of heat shock protein hps70 gene), as integrated in the P-element sequence in such a manner that the downstreams are in opposite directions. Compared with conventional such vectors (Proc. Natl. Acad. Sci. USA 93:12418–12422, 1996; Dros. Inf. Serv. 80:90–92, 1997), the inventive method using such two sets of the expression regulatory sequence can permit the emergence of a mutant phenotype at a two-fold frequency. Such GS vector can be prepared from for example P-element transformation vector pCaSpeR3 (Gene 74:445–456, 1988). Using pCaSpeR3, two sets of the expression regulatory sequence can be inserted individually in the multicloning site on the 3'P-element side, but preferably, one set of the expression regulatory sequence is inserted in a P transposase-encoding region appropriately prepared on the side of 5'P-element. A marker gene is integrated between the two sets of the expression regulatory sequence. The marker gene, a causative gene of the change in the Drosophila phenotypes, can accomplish ready screening of an individual with the GS vector integrated in the genome thereof, on the basis of the change in the phenotypes. As the marker gene, appropriate ones such as white gene in FIG. 1a can be used.

The GS vector is recommended to be constructed at a full length below 8 kbp, more preferably at a full length of 5 to 6 kbp. The vector of a smaller size enables the improvement of the insertion efficiency, to raise the frequency of the occurrence of a mutant phenotype.

By the method of such composition described above, the GS vector prepared below in Example 1 can allow the emergence of a phenotype at a frequency about 10-fold the frequency caused by the vector prepared by the conventional method (Proc. Natl. Acad. Sci. USA 93:12418–12422, 1996).

Figure 1B:
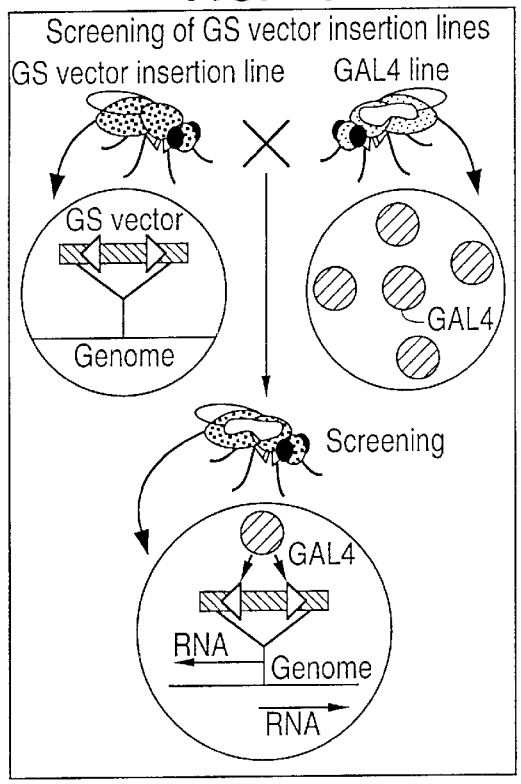

According to the method of the present invention, the GS vector thus prepared is inserted in the genome of Drosophila to create plural GS vector insertion lines. The GS vector is randomly inserted in various Sites of the genome, owing to the presence of the P-element. As shown in FIG. 1b. then, the GS vector insertion lines and the GAL4 expression lines are mated. Various lines are known as the GAL4 expression lines, so one of such lines is appropriately selected.

In the progeny individuals from the mating, the sequences downstream the GS vector insertion sites are compulsively transcribed and expressed in the GAL4 expressing tissues. Then, the full-length mRNA is transcribed when the GS vector insertion site is located on 5' side of the gene; and antisense RNA and mRNA encoding an incomplete-length protein are transcribed when the GS vector insertion site is located inside the gene; antisense RNA is transcribed when the GS vector insertion site is located on the 3' side of the gene. Further, the biological actions of these transcription products are exerted as phenotypic changes in the progeny individuals. Sense-chain transcription is exerted as a phenotype with functional acquisition due to the ectopic expression of the resulting translation product; and antisense RNA transcription is exerted as a functionally defective phenotype due to the inhibition of the translation of a wild-type product. Additionally, a partially defective protein generated indicates the occurrence of a mutant of a type, dominant active or dominant negative. The site and timing with the occurrence of forced expression depend on the expression specificity of GAL4. By selecting a GAL4 expression line for mating, forced expression can be induced, in a manner specific to the specific tissue or timing.

Because the function of a gene significantly varies, depending on the cell biological background for the expression of the gene, additionally, a conventionally unknown potential function of the gene can sometimes be exhibited, for the first time, when the gene is compulsively expressed at a site different from the essential expression site.

Figure 1C:
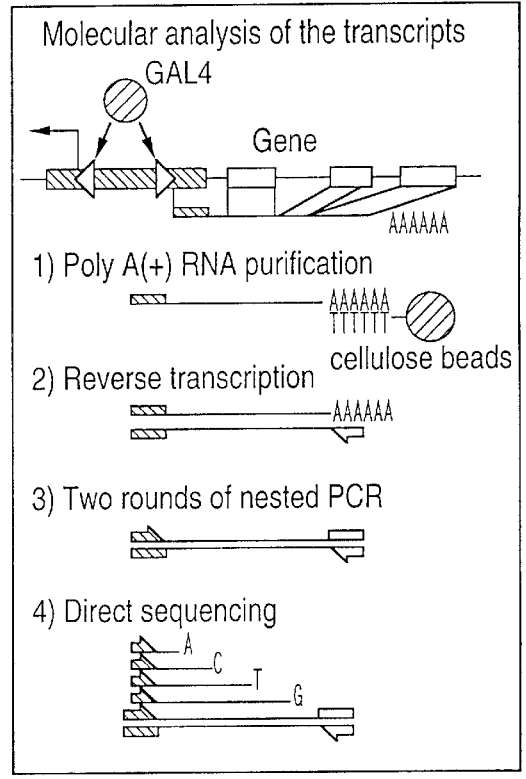

According to the method of the present invention, a novel gene can be detected by isolating a causative gene on the basis of a mutant phenotype recovered by compulsive expression. As shown in FIG. 1c, for example, the gene can be detected by amplifying the compulsively expressed mRNA by reverse-transcriptase-polymerase chain reaction method (RT-PCR) and isolating the DNA sequence from the resulting PCR product. As the RT-PCR template, a mRNA fragment comprising a partial sequence of the GS vector is satisfactorily isolated by using polyA(+) RNA.

According to the method of the present invention, the GS vector-inserted individuals are used as they are for the bioassay for the screening of all the biological functions such as development, growth, behavior and life span, to cover the detection of novel genes involved in the biological functions. Using the Drosophila gene thus detected or a partial sequence thereof as probe, a homologous gene can be isolated from the genome library of an organism other than Drosophila, the cDNA library thereof or the whole genome sequence information. Otherwise, a homologous gene can be amplified and isolated by PCR using the genome DNA or cDNA of an organism other than Drosophila.

The invention will now be described in more detail in more concrete manner in the following Examples, but the invention is not limited to these Examples.

EXAMPLE 1

According to the gene search method of the present invention, the GS vector was inserted in Drosophila, to prepare GS vector insertion lines.

1. Construction of GS Vector

By inducing a mutation in P-element transformation vector pCaSpeR3 (Gene 74:445–456, 1988) by means of PCR, EcoRI site was prepared in the P transposase-encoding region in the vicinity of the 5'P terminus. Five tandem repeats of UAS conjugated with a core promoter derived from the gene hps70 of pUAST (Development 118: 401–415, 1993) were inserted at the EcoRI site in the vicinity of the 5' P terminus and the XhoI site at the multicloning site in the vicinity of the 3' P terminus, to prepare GS vector of a schematic structure shown in FIG. 1a. The GS vector of its 5245-bp full length carries the white gene as a marker gene between 2 sets of UAS enhancer/promoter.

2. Preparation of GS Vector Insertion Lines

The GS vector prepared above in 1 was introduced in Drosophila (yw line; supplied from the Tokyo Metropolitan University), to prepare the transgenic Drosophila. By using a transposase delta2–3, subsequently, the GS vector was transposed, to prepare GS vector insertion lines of 613 in number. The transposed GS vector was located in the chromosome X in 147 lines, the chromosome 2 in 226 lines, the chromosome 3 in 237 lines and the chromosome 4 in 3 lines. Additionally, at least one detectable phenotype (for example, lethality and defective adult structure) could be detected in 394 lines (64%).

EXAMPLE 2

Among the GS vector insertion lines prepared in Example 1, 163 lines randomly selected from the 394 lines with any detectable phenotype were mated with the GAL4 expression lines to generate progeny (F1) individuals, which were then allowed to express transcription products by the GAL4 transcription activator. The resulting transcription products were analyzed. Herein, dpp-GAL4, sev-GAL4, hs GAL4, 29BD-GAL4 and c355-GAL4 (all supplied by the Bloomington Stock Center) were used as the GAL4 expression lines.

1. Identification Method of Transcription Products

Fly larvae of age 3 days from the F1 individual between the GS vector insertion lines and the hs GAL4 line as prepared in Example 1.2 were placed at a ratio of 20–30 fly larvae per tube in 1.5-ml tubes, which were then warmed at 37° C. for one hour. From the larvae was isolated polyA(+) RNA by using Quick prep micro mRNA purification kit (manufactured by Amersham Pharmacia Biotech Co. Ltd.), which was subjected to mRNA reverse-transcription by using First-strand cDNA synthetic kit (manufactured by Amersham Pharmacia Biotech Co. Ltd.). Using 1 μl of the resulting mRNA as template, 5' P-and 3' P transcription products were amplified by PCR with an enzyme mixture ELONGASE (manufactured by GIBCO BRL INC.). The total volume of the PCR solution was 50 μl. Using as PCR primers the upstream common primer (SQ ID No. 1) and NotI-terminated oligo-d(T) primer (SQ ID No. 2), cDNA was synthetically prepared. Subsequently, 1 μl of the first PCR product was added to the PCR solution in total of 50 μl, to separately amplify the 5' P transcription product and the 3' P transcription product. As the PCR primers, an upstream primer 5' P-specific primer (SQ ID No. 3) or 3' P-specific primer (SQ ID No. 4) and a downstream primer (SQ ID No. 5) were used. By using an auto-analyzer Perkin Elmer Gene Amp PCR System 2400 or 9700, PCR was carried out under the following cycling conditions: 94° C. (60 seconds); 16 cycles of 94° C. (15 seconds) and 65° C. (10 minutes); 12 cycles of 94° C. (15 seconds) and 65° C. (10 minutes; the duration is prolonged by 15 seconds per one cycle); and 72° C. (10 minutes). After termination of all the cycles, the resulting solution was retained at 4° C. The resulting PCR products were electrophoresed on 1.0% agarose (Sigma type II) gel; bands of the amplified products were cut out with a knife; and the PCR products were purified by QIAEX II gel extraction kit (manufactured by QIAGEN Co.). Along with ABI PRISM Cycle Sequencing Kit (manufactured by Perkin Elmer Co.), the purified DNA fragments were subjected to sequencing by using a 5'-P/3'-P common primer (SQ ID No. 6) by an auto-analyzer ABI PRISM GENETIC Analyzer 310 (manufactured by Perkin Elmer Co.).

The sequence analogy was screened on the basis of the NCBI non-redundant nucleic acid data base and the dbest or NCBI non-redundant protein data base by using the program BLASTN or BLASTX (Proc. Natl. Acad. Sci. USA 87:5509–5513, 1990).

2. Analysis of Transcription Products

Because the P-element induces the occurrence of the repetition of the 8-bp target sequence at the inserted site (Cell 34:25–35, 1983), two different transcription products derived from the single insertion of the P-element can readily be identified due to the presence of the common first (5'-terminal) 8 base pairs. Because 8 GS vector insertion lines expressed two transcription products with different terminal sequences, it was verified that two P-elements were inserted in the same one chromosome. Owing to the P-element insertion including such double insertion, transcription products in total of 171 were identified in the same manner as in 1 and were then used for screening with data base.

The results shown in Table 1 indicate that 47% of the sequenced transcription products corresponded to known sequences.

TABLE 1

|  | Number of insertions | % |
|---|---|---|
| Known Sequences* |  |  |
| known genes | 35 | 20 |
| ESTs | 33 | 19 |
| STSa | 6 | 4 |
| Transposons or repetitive sequences | 7 | 4 |
| Novel sequences |  |  |
| Homolog | 2 | 1 |
| Novel | 88 | 51 |
| Total | 171 | 100 |

*Similarity scores for the known genes and ESTs are shown in Table 2.

The site of P-element insertion was examined in the transcription initiation sites of known genes and the known ESTs (Expressed Sequence Tags). The P-element insertion site was determined, relative to a known mRNA 5' terminus designated +1. The results are shown in Table 2 (known genes) and Table 3 (ESTs). 50% of the sites of P-element insertion were located at positions −150 to +100. Specifically, the sites were located most frequently at positions −100 to −1. In terms of the relation with known genes, P-element was inserted upstream the protein-encoding regions of 83% of the known genes, suggesting that many of the phenotypes detected by the screening were due to the excessive expression or ectopic expression of the full-length mRNA.

TABLE 2

| | Inserted locus Known genes | | | | |
|---|---|---|---|---|---|
| GS line | Full name | Symbol | Accession | Score | Insertion Site* |
| 97 | Transcription-factor-ll-S | TfllA-S | X83271 | <1e-100 | −677 |
| 1029 | Netrin-B | NetB | U60317 | 1e-24 | −95 |
| 1032 | polyhomeotic | ph | M64750 | <1e-100 | −353 |
| 1038 | raspberry | ras | L14847 | <1e-100 | −666 |
| 1053 | amnesiac | amn | U22825 | <1e-100 | +2597 |
| 1069 | Fasciclin 2 | Fas2 | M77165 | 4e-69 | −63 |
| 1073 | wings apart-like | wapl | U40214 | 2e-84 | −117 |
| 1091 | embryonic lethal, abnormal version | elav | M21153 | <1e-100 | −450 |
| 1115 | bang senseless | bss | X89811 | <1e-100 | +364 |
| 1131 | Actin 5C | Act5C | X15730 | <1e-100 | −923 |
| 1141 | armadillo | arm | X54468 | <1e-100 | intron |
| 1144 | ovo | ovo | X59772 | <1e-100 | −58 |
| 2011 | High mobility protein D | HmgD | M77023 | <1e-100 | −66 |
| 2042 | High mobility protein D | HmgD | M77023 | <1e-100 | −10 |
| 2115 | exuperantia | exu | S72757 | <1e-100 | 3' flanking region |
| 2120 | fuzzy | fy | AF022891 | <1e-100 | −196 |
| 2137 | High mobility protein D | HmgD | M77023 | 2e-11 | intron |
| 2141 | string of pearls | sop | U01335 | 9e-21 | −35 |
| 2160 | Glutathione S trasferase 2 | Gst2 | M95198 | <1e-100 | +10 |
| 2163B | ornithine decarboxylase antizyme | | AF038597 | <1e-100 | intron |
| 2220 | exuperantia | exu | S72757 | <1e-100 | 3' flanking region |
| 2227 | anterior open | aop | M97694 | <1e-100 | −97 |
| 2228 | expanded | ex | L14768 | <1e-100 | +617 |
| 3026 | tramtrack | ttk | Z11723 | 2e-35 | −3 |
| 3029 | Dihydroorotate dehydrogenase | Dhod | L00964 | 3e-37 | −277 |
| 3052 | Histone H2A variant | His2AvD | X07485 | <1e-100 | intron |
| 3069 | tramtrack | ttk | Z11723 | 1e-43 | intron |
| 3089 | neuralized | neur | S62597 | <1e-100 | +24 |
| 3097 | modifier of mdg4 | mod(mdg4) | U30905 | <1e-100 | intron |
| 3120 | string | stg | X57495 | 3e-92 | −135 |
| 3127 | Histone H2A variant | His2AvD | X07485 | <1e-100 | +2 |
| 3129 | stonewall | stwl | U41367 | <1e-100 | −111 |
| 3165 | tramtrack | ttk | X71626 | 1e-15 | −416 |
| 3205 | neuralized | neur | X61617 | <1e-100 | −69 |
| 3230 | groucho | gro | M20571 | 6e-76 | intron |

*Transcription start site (+1) of each known gene was defined as the 5' most ends of mRNA sequence reported so far. The vector insertion sites was determined based on the sequence of the 5' end of induced transcripts.

TABLE 3

| | Insertion locus | | | |
|---|---|---|---|---|
| GS line | ESTs | Accession | Score | Insertion site* |
| 1027 | LD12308 | AA438512 | 2e-63 | −93 |
| 1084 | LD12308 | AA438512 | 1e-63 | −93 |
| 1135 | LD22118 | AA817082 | <1e-100 | −74 |
| 2002 | LD29847 | AA949818 | <1e-100 | −37 |
| 2003 | LD27171 | AA941860 | <1e-100 | +290 |
| 2007 | LD06340 | AA263242 | 8e-25 | −250 |
| 2025 | LD12957 | AA438639 | 3e-88 | +37 |
| 2038 | LD01639 | AA735228 | <1e-100 | −29 |
| 2048A | LD03829 | AA201147 | 2e-49 | +101 |
| 2048B | LD07122 | AA263935 | 3e-30 | −19 |
| 2053 | LD04728 | AA201504 | <1e-100 | −3 |
| 2055 | LD03274 | AA390332 | <1e-100 | −51 |
| 2067 | GM02209 | AA567240 | <1e-100 | +56 |
| 2074 | LD03274 | AA390332 | <1e-100 | −51 |
| 2091 | LD03274 | AA390332 | <1e-100 | −51 |
| 2121 | LD29214 | AA952141 | 3e-49 | +35 |
| 2138 | LD04967 | AA201761 | 6e-53 | +362 |
| 2163A | LD04971 | AA201765 | <1e-100 | −6 |
| 2191 | LD06340 | AA263242 | 6e-82 | −275 |
| 2202 | LD14959 | AA440376 | <1e-100 | intron |
| 2207A | GM09451 | AA697215 | 1e-64 | −275 |
| 2207B | LD06340 | AA263242 | 8e-25 | −255 |
| 2208 | LD20843 | AA541057 | 4e-62 | −11 |
| 2209 | LD33989 | AA979429 | <1e-100 | +6 |
| 3005 | LD09360 | AA390491 | <1e-100 | −1 |
| 3011 | LD25593 | AA941450 | <1e-100 | +64 |
| 3028 | GM10514 | AA803288 | <1e-100 | +64 |
| 3082 | LD14744 | AA440145 | <1e-100 | intron |
| 3086 | HL04053 | AA698259 | 4e-92 | intron |
| 3087 | LD32772 | AA951892 | 2e-29 | −34 |
| 3130 | LD02456 | AA202301 | 6e-26 | within |
| 3199 | LD21713 | AA735667 | <1e-100 | −56 |
| 3219 | LD07107 | AA263927 | <1e-100 | within |

*Transcription start site (+1) of each EST and the vector insertion sites were determined in the same manner as in Table 2

By the screening, furthermore, two novel Drosophila genes with sequences analogous to human genes were detected. More specifically, the Drosophila genes were analogous to human Ras associated protein 2 (Ras2) gene (Oncogene 3:201–204, 1988) and human microsome glutathione S-transferase (mGST) gene (J. Biol. Chem. 263:8430–8436, 1988). The amino acid sequences of proteins speculated from these Drosophila genes are shown in FIG. 2, compared with the amino acid sequences of the proteins encoded by the human genes.

Additionally, these novel Drosophila genes were inserted upstream the protein-encoding region; after mating with sev-GAL4 line, these genes were expressed excessively and detected as rough eye phenotype.

As has been described above, the invention provides a gene search method comprising P-element insertion and being capable of efficiently identifying a novel gene regulating various biological functions of Drosophila and specifying a function corresponding to the novel gene.

What is claimed is:

1. A vector comprising a pair of Drosophila P-element sequences and two sets of an expression regulatory sequence integrated in the P-element sequences, wherein the expression regulatory sequence comprises a UAS sequence for GAL4 transcription activator and a promoter sequence, and wherein the transcription orientations of the expression regulatory sequences for their downstream sequences are in opposite directions.

2. The vector according to claim 1, wherein the promoter sequence is a core promoter sequence of a gene encoding heat shock protein hsp70.

3. The vector according to claim 1, wherein the two sets of the expression regulatory sequence are independently integrated in a 5' P-element sequence and a 3' P-element sequence.

4. The vector according to claim 1, which further comprises a marker gene between the two sets of the expression regulatory sequence.

5. The vector according to claim 4, wherein the marker gene is a Drosophila white gene.

6. The vector according to claim 1, wherein the full length of the vector is less than 8 kb.

7. A transgenic Drosophila whose genome comprises the vector of claim 1.

8. A method for identifying an unknown gene of Drosophila, said method comprising:
   (a) generating a transgenic Drosophila whose genome comprises the vector of claim 1,
   (b) mating the transgenic Drosophila with a Drosophila expressing a GAL4 transcription activator to create progenies, and identifying a vector-inserted line with a phenotype different from those of the parental Drosophila, and
   (c) determining the nucleotide sequence of the gene whose forced; expression or misexpression is responsible for the phenotype of the mutant individual.

9. The method according to claim 8, wherein, in step (c), a mRNA fragment comprising mRNAs transcribed from a partial sequence of said vector is amplified by a reverse transcriptase polymerase chain reaction method, the amplified DNA is isolated and purified, and then the purified DNA is subjected to sequencing analysis with appropriate primers to determine the nucleotide sequence of the gene.

* * * * *

```
                             SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 1
ctgaataggg aattgggaat tcg                                              23

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 2
aactggaaga attcgcggcc gcaggaattt tttttttttt ttttt                      45

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 3
gtgtatactt cggtaagctt cg                                               22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 4
attgcaagca tacgttaagt gga                                              23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 5
agaactggaa gaattcgcgg                                                  20

<210> SEQ ID NO 6
<211> LENGTH: 21
<212> TYPE: DNA
```

-continued

```
<213> ORGANISM: Artificial Sequence
<220> FEATURE:
<223> OTHER INFORMATION: Description of Artificial Sequence: SYNTHESIZED
      OLIGONUCLEOTIDE

<400> SEQUENCE: 6
cgacgggacc accttatgtt a                                            21

<210> SEQ ID NO 7
<211> LENGTH: 182
<212> TYPE: PRT
<213> ORGANISM: Drosophila melanogaster

<400> SEQUENCE: 7

Met Arg Glu Phe Lys Val Val Leu Gly Ser Gly Gly Val Gly Lys
  1               5                  10                  15

Ser Ala Leu Thr Val Gln Phe Val Ser Gly Cys Phe Ile Glu Lys Tyr
                 20                  25                  30

Asp Pro Thr Ile Glu Asp Phe Tyr Arg Lys Glu Ile Glu Val Asp Ser
                 35                  40                  45

Ser Pro Cys Val Leu Glu Ile Leu Asp Thr Ala Gly Thr Glu Gln Phe
         50                  55                  60

Ala Ser Met Arg Asp Leu Tyr Ile Lys Asn Gly His Gly Phe Ile Val
 65                  70                  75                  80

Met Tyr Ser Leu Thr Asn His Gln Thr Phe Gln Asp Ile Ser Ser Met
                 85                  90                  95

Lys Asn Val Ile Thr Arg Val Lys Gly Ser Gln Pro Ala Pro Ile Leu
                100                 105                 110

Leu Val Ala Asn Lys Phe Asp Leu Asp Cys Gln Arg Glu Val Ser Thr
            115                 120                 125

Ala Glu Gly Asn Ala Leu Ala Gln Leu Trp Asp Cys Pro Phe Ile Glu
        130                 135                 140

Ala Ser Ala Lys Asp Arg Ile Asn Val Asn Glu Val Phe Ala Thr Ile
145                 150                 155                 160

Val Arg Glu Met Asn Leu Thr Gln Glu Asn Arg Gln Lys Lys Asn Tyr
                165                 170                 175

Cys Cys Cys Thr Leu Leu
            180

<210> SEQ ID NO 8
<211> LENGTH: 183
<212> TYPE: PRT
<213> ORGANISM: Homo sapiens

<400> SEQUENCE: 8

Met Arg Glu Tyr Lys Val Val Leu Gly Ser Gly Gly Val Gly Lys
  1               5                  10                  15

Ser Ala Leu Thr Val Gln Phe Val Thr Gly Thr Phe Ile Glu Lys Tyr
                 20                  25                  30

Asp Pro Thr Ile Glu Asp Phe Tyr Arg Lys Glu Ile Glu Val Asp Ser
                 35                  40                  45

Ser Pro Ser Val Leu Glu Ile Leu Asp Thr Ala Gly Thr Glu Gln Phe
         50                  55                  60

Ala Ser Met Arg Asp Leu Tyr Ile Lys Asn Gly Gln Gly Phe Ile Leu
 65                  70                  75                  80

Val Tyr Ser Leu Val Asn Gln Gln Ser Phe Gln Asp Ile Lys Pro Met
                 85                  90                  95
```

-continued

Arg Asp Gln Ile Ile Arg Val Lys Arg Tyr Glu Lys Val Pro Val Ile
            100                 105                 110

Leu Val Gly Asn Lys Val Asp Leu Glu Ser Glu Arg Glu Val Ser Ser
            115                 120                 125

Ser Glu Gly Arg Ala Leu Ala Glu Glu Trp Gly Cys Pro Phe Met Glu
130                 135                 140

Thr Ser Ala Lys Ser Lys Thr Met Val Asp Glu Leu Phe Ala Glu Ile
145                 150                 155                 160

Val Arg Gln Met Asn Tyr Ala Ala Gln Pro Asp Lys Asp Asp Pro Cys
                165                 170                 175

Cys Ser Ala Cys Asn Ile Gln
            180

<210> SEQ ID NO 9
<211> LENGTH: 152
<212> TYPE: PRT
<213> ORGANISM: Drosophila melanogaster

<400> SEQUENCE: 9

Met Ala Ser Pro Val Glu Leu Leu Ser Leu Ser Asn Pro Val Phe Lys
1               5                   10                  15

Ser Phe Thr Phe Trp Val Gly Val Leu Val Ile Lys Met Leu Leu Met
            20                  25                  30

Ser Leu Leu Thr Ala Ile Gln Arg Phe Asn Thr Lys Thr Phe Ala Asn
        35                  40                  45

Pro Glu Asp Leu Met Ser Pro Lys Leu Lys Val Lys Phe Asp Asp Pro
    50                  55                  60

Asn Val Glu Arg Val Arg Arg Ala His Arg Asn Asp Leu Glu Asn Ile
65                  70                  75                  80

Leu Pro Phe Phe Ala Ile Gly Leu Leu Tyr Val Leu Thr Asp Pro Ala
                85                  90                  95

Ala Phe Leu Ala Ile Asn Leu Phe Arg Ala Val Gly Ile Ala Arg Ile
            100                 105                 110

Val His Thr Leu Val Tyr Ala Val Val Val Pro Gln Pro Ser Arg
            115                 120                 125

Ala Leu Ala Phe Phe Val Ala Leu Gly Ala Thr Val Tyr Met Ala Leu
130                 135                 140

Gln Val Ile Ala Ser Ala Ala Phe
145                 150

<210> SEQ ID NO 10
<211> LENGTH: 155
<212> TYPE: PRT
<213> ORGANISM: Homo sapiens

<400> SEQUENCE: 10

Met Val Asp Leu Thr Gln Val Met Asp Asp Glu Val Phe Met Ala Phe
1               5                   10                  15

Ala Ser Tyr Ala Thr Ile Ile Leu Ser Lys Met Met Leu Met Ser Thr
            20                  25                  30

Ala Thr Ala Phe Tyr Arg Leu Thr Arg Lys Val Phe Ala Asn Pro Glu
        35                  40                  45

Asp Cys Val Ala Phe Gly Lys Gly Glu Asn Ala Lys Lys Tyr Leu Arg
    50                  55                  60

Thr Asp Asp Arg Val Glu Arg Val Arg Arg Ala His Leu Asn Asp Leu
65                  70                  75                  80

```
-continued

Glu Asn Ile Ile Pro Phe Leu Gly Ile Gly Leu Leu Tyr Ser Leu Ser
                 85              90              95

Gly Pro Asp Pro Ser Thr Ala Ile Leu His Phe Arg Leu Phe Val Gly
            100             105             110

Ala Arg Ile Tyr His Thr Ile Ala Tyr Leu Thr Pro Leu Pro Gln Pro
        115             120             125

Asn Arg Ala Leu Ser Phe Phe Val Gly Tyr Gly Val Thr Leu Ser Met
    130             135             140

Ala Tyr Arg Leu Leu Lys Ser Lys Leu Tyr Leu
145             150             155
```